(12) United States Patent
Braver et al.

(10) Patent No.: US 9,566,420 B2
(45) Date of Patent: Feb. 14, 2017

(54) MEDICAL INSTRUMENTS OF TREATING AND/OR DIAGNOSING OF ANORECTAL DISORDERS, AND DEVICES AND METHODS FOR INSERTION OF SUCH

(75) Inventors: David Braver, Jerusalem (IL); Iris Shahar, RaAnana (IL)

(73) Assignee: Ocure Ltd., Jerusalem (IL)

( * ) Notice: Subject to any disclaimer, the term of this patent is extended or adjusted under 35 U.S.C. 154(b) by 132 days.

(21) Appl. No.: 13/818,692

(22) PCT Filed: Aug. 25, 2011

(86) PCT No.: PCT/IL2011/000689
§ 371 (c)(1),
(2), (4) Date: Feb. 25, 2013

(87) PCT Pub. No.: WO2012/025930
PCT Pub. Date: Mar. 1, 2012

(65) Prior Publication Data
US 2013/0158395 A1    Jun. 20, 2013

Related U.S. Application Data

(60) Provisional application No. 61/376,710, filed on Aug. 25, 2010.

(51) Int. Cl.
*A61M 31/00* (2006.01)
(52) U.S. Cl.
CPC ........... *A61M 31/002* (2013.01); *A61M 31/00* (2013.01); *A61M 31/005* (2013.01); *A61M 31/007* (2013.01); *A61M 2210/1067* (2013.01)
(58) Field of Classification Search
CPC ..................... A61M 2210/1067; A61M 31/00; A61M 31/002; A61M 31/007; A61M 2025/1088; A61K 9/02; A61K 9/025; A61K 9/031; Y10S 424/15; A61F 13/2015; A61F 13/2054–13/2068; A61F 5/0093; A61F 2013/15113; A61F 13/2011; A61F 13/2028; A61F 13/2025; A61F 13/2071; A61F 13/2074; A61F 2013/8473; A61F 2/00
See application file for complete search history.

(56) References Cited

U.S. PATENT DOCUMENTS 1,561,020 A * 11/1925 Pond ...................... A61F 5/0093
                                                    604/287
3,433,225 A *  3/1969 Voss ........................ A61F 13/26
                                                     604/14
(Continued)

FOREIGN PATENT DOCUMENTS

IL    WO 2009107136 A2 *  9/2009  .......... A61M 31/002
WO    WO 2007/077551         7/2007
(Continued)

OTHER PUBLICATIONS

Communication Relating to the Results of the Partial International Search Dated Dec. 22, 2011 From the International Searching Authority Re. Application No. PCT/IL2011/000689.
(Continued)

*Primary Examiner* — Nathan R Price
*Assistant Examiner* — Weng Lee (57) ABSTRACT

A medical instrument for treating and/or diagnosing anorectal disorders which comprises a slender member that is sized and shaped for being placed in the anal canal of a patient, along at least a portion of the anal sphincter, so that an outer surface of the slender member is in contact with inner walls of the anal canal.

23 Claims, 9 Drawing Sheets

(56) References Cited

U.S. PATENT DOCUMENTS

| | | | |
|---|---|---|---|
| 3,512,527 A * | 5/1970 | Marguerite | A61F 5/0093 604/285 |
| 3,777,755 A | 12/1973 | Groves | |
| 3,865,108 A | 2/1975 | Hartop | |
| 3,916,898 A * | 11/1975 | Robinson | A61K 9/0036 424/433 |
| 3,993,072 A * | 11/1976 | Zaffaroni | A61M 31/002 128/833 |
| 4,249,531 A | 2/1981 | Heller et al. | |
| 4,402,693 A | 9/1983 | Roseman et al. | |
| 5,800,338 A * | 9/1998 | Kollerup | A61F 13/202 600/29 |
| 5,993,374 A | 11/1999 | Kick | |
| 2004/0249364 A1 | 12/2004 | Kaploun | |
| 2005/0058714 A1 * | 3/2005 | Beebe | A61M 31/002 424/489 |
| 2007/0202151 A1 * | 8/2007 | Lee | A61K 9/0034 424/426 |

FOREIGN PATENT DOCUMENTS

| | | | |
|---|---|---|---|
| WO | WO 2007/094004 | 8/2007 | |
| WO | WO 2009/107136 | 9/2009 | |
| WO | WO 2009107136 A2 * | 9/2009 | A61M 31/00 |
| WO | WO 2012/025930 | 3/2012 | |

OTHER PUBLICATIONS

International Preliminary Report on Patentability Dated Mar. 7, 2013 From the International Bureau of WIPO Re. Application No. PCT/IL2011/000689.

International Search Report and the Written Opinion Dated Feb. 21, 2012 From the International Searching Authority Re. Application No. PCT/IL2011/000689.

* cited by examiner

MEDICAL INSTRUMENTS OF TREATING AND/OR DIAGNOSING OF ANORECTAL DISORDERS, AND DEVICES AND METHODS FOR INSERTION OF SUCH

RELATED APPLICATIONS

This application is a National Phase of PCT Patent Application No. PCT/IL2011/000689 having International filing date of Aug. 25, 2011, which claims the benefit of priority under 35 USC §119(e) of U.S. Provisional Patent Application No. 61/376,710 filed on Aug. 25, 2010. The contents of the above applications are all incorporated by reference as if fully set forth herein in their entirety.

FIELD AND BACKGROUND OF THE INVENTION

Present invention relates to devices and methods for the treatment and/or diagnosis of anorectal disorders, and more particularly to device and method of treating and/or diagnosing of anorectal disorders by using a medical instrument which is inserted into the anal canal by an applicator.

The anal sphincter includes internal and external portions. The internal anal sphincter is a ring of smooth muscle which surrounds the lower extremity of the rectum and is formed by an aggregation of the involuntary smooth muscle fibers. The internal anal sphincter is under a state of chronic contraction, due both to intrinsic myogenic properties and external innervation. The external anal sphincter is a thin flat plane of striated muscle fibers, under voluntary control, adherent to the integument surrounding the margin of the anus.

Anorectal disorders include anal sphincter spasm, anal fissures, abscesses, fistulae, ulcers, irritation and itching (pruritus ani), hemorrhoids, incontinence, constipation, inflammation, infection, and cancer. Anal sphincter spasm is a condition in which the muscles of the internal anal sphincter are under abnormal tension. This may be caused, for example, by local inflammation. The strong contractions of the internal anal sphincter associated with sphincter spasm often give rise to mucosal ischaemia, resulting in anal fissures, which are painful linear ulcers or crack-like tears in the distal anal canal, which, in the short-term, usually involves only the epithelium and, in the long-term, involves the full thickness of the anal mucosa. Because of the pain of a fissure, the internal anal sphincter may go into spasm, raising pressure within the anus.

Anorectal disorders which involve ulcer or crack in the folds of the anal margin, for example anal fissures, may not be promptly heal because of the high internal anal sphincter spasm and reduction in vascular perfusion at the site. Acute anal fissures which do not heal over time become chronic anal fissures or anal ulcers. Current treatments of chronic anal fissures are directed at relieving sphincter spasm and include dilatation (under anesthesia), or cutting the sphincter (lateral internal sphincterotomy) to reduce the hypertonicity of the internal anal sphincter muscle.

Some devices have been developed for treating anorectal disorders, for example Int. Patent Application No. PCTIIL2006/001446, filed on Dec. 14, 2006, describes a rectally insertable device for localized drug delivery to the anal sphincter of a subject. The device comprises a shell for containing an active pharmaceutical ingredient, the shell being substantially impermeable to the active pharmaceutical ingredient wherein a lower portion of the shell is configured to release the active pharmaceutical ingredient from the shell and wherein when the device is inserted into the rectum of the subject, the lower portion of the shell is proximal to the anal sphincter, such that the active pharmaceutical ingredient is released proximal to the anal sphincter.

Another example is described in International Patent Publication Number WO 2007/094004, which describes a device for prolonged delivery of an active agent to a body cavity. The device is insertable into the cavity of a subject in need. The device includes a non-absorbable, flexible tube of an elongated shape, a removable core element situation within the tube, and a retention mechanism for maintaining the device within the cavity.

SUMMARY OF THE INVENTION

According to some embodiments of the present invention there is provided a medical instrument for treating and/or diagnosing anorectal disorders. The medical instrument comprises a slender member sized and shaped for being placed in the anal canal of a patient, along at least a portion of the anal sphincter, so that an outer surface of the slender member is in contact with inner walls of the anal canal.

Optionally, the slender member the slender member contains an active agent for a sustained release along the portion.

More optionally, the active agent is selected from a group consisting of analgesic, anthelmintic, antibacterial, antiviral, antimicrobial, antiprotozoal, antidiarrheal, antihemorrhoidal, antihemorrhoidal, hemostatic, anti-inflammatory, a diagnostic aid, a disinfectant, antifungal, an alkylating agent, muscle relaxants, oxygen enrichment, vasodilators, anti-ischemic agents, chemical debridement, hormones, growth factors, cytokines and other bioactive peptidic compounds, an antacid, a sedative, a mucolytic a contrast media, an antidote, metabolic/endocrinal preparation and an anti-cancer agent.

Optionally, the medical instrument further comprises a cover layer substantially circumferentially covering an outer surface of the slender member, the slender member having a diameter set to push the cover layer toward the inner walls.

More optionally, the medical instrument further comprises an anchoring element, placed above the distal end of the slender member; the anchoring element is wider than the slender member when disposed in the anal canal.

Optionally, the medical instrument further comprises a thread connected to the slender member so as to allow pulling out the slender member by the patient.

Optionally, the slender member comprising a plurality of sub elements threaded on a common thread.

More optionally, at least one of the cover layer and the slender member is at least one of soaked, covered and laminated with an active agent.

More optionally, at least one of the cover layer and the slender member is at least one of soaked, covered and laminated with at least one diagnostic agent.

Optionally, the medical instrument further comprises a dissolvable shell sized to cover at least a distal end of the slender member.

Optionally, the slender member is expandable and the diameter is achieved when the slender member is in an expanded state.

According to some embodiments of the present invention there is provided an insertion device of inserting a medical instrument of treating or diagnosing an anorectal disorders. The insertion device comprises a tubular member sized for placement in the anal canal, at least along the anal sphincter and having a longitudinal lumen and a distal end and an applicator pivotally movable within the longitudinal lumen toward the distal end so as to push at least a distal portion of a medical instrument via the distal end, the medical instrument being insertable within the longitudinal lumen and sized for being substantially placed in the anal canal along the anal sphincter.

Optionally, the applicator has an inner lumen which is sized for surrounding at least a proximal portion of the medical instrument.

Optionally, the medical instrument is an expandable slender member substantially circumferentially covered by a cover layer.

Optionally, the distal end having a rounded tip.

Optionally, the insertion device further comprises at least one blocking element mounted on the circumferential outer surface of the tubular member so as to locate the distal end above the anal dentate line when the tubular member is placed in the anal canal.

Optionally, the distal end has a first average diameter and the rest of the tubular member having a second average diameter, the first average diameter being smaller than the second average diameter.

Optionally, the distal end having a tip with at least one flexible flap configured for being pushed by the medical instrument when the medical instrument being extracted from the tip.

Optionally, the at least one flexible flap form a semi rigid structure which does not substantially collapse when the tubular member is placed in the anal canal.

Optionally, the at least one flexible flap is rounded.

According to some embodiments of the present invention there is provided a method of inserting a medical instrument of treating and/or diagnosing an anorectal disorders. The method comprises providing an insertion device having a tubular member sized for placement in an anal canal, along at least a portion of the anal sphincter, and a medical instrument placed within the tubular member, placing the tubular member in the anal canal so that a distal tip thereof being located above the anal dentate line, pushing the medical instrument from a longitudinal lumen of the tubular member to extract at least a distal portion thereof from the distal end in the anal canal, and pulling the tubular member and from the anal canal while leaving the medical instrument along at least a portion of the anal sphincter.

Optionally, the pushing comprises pivotally moving an applicator in the longitudinal lumen so as to extract at least the distal portion from the distal end.

Optionally, the pushing further comprises deflecting at least one flap in the distal end.

Optionally, the method further comprises bandaging, during the pulling, the inner walls of the portion by the outer surface of the medical instrument.

According to some embodiments of the present invention, there is provided a medical instrument for treating and/or diagnosing anorectal disorders. The medical instrument comprises a slender member sized and shaped for being placed in the anal canal of a patient, along at least a portion of the anal sphincter, an active agent disposed in the slender member, and a cover layer substantially circumferentially covering an outer surface of the slender member and perforated with a plurality of apertures. The apertures are set so as to allow a release of the active agent therethrough.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Present invention relates to devices and methods for the treatment and/or diagnosis of anorectal disorders, and more particularly to device and method of treating the anal sphincter by using a medical device which is inserted to the anal canal by an applicator.

According to an aspect of some embodiments of the present invention there is provided a medical instrument for treating and/or diagnosing anorectal disorders. The medical instrument includes a slender member that is sized and shaped for being placed in the anal canal, along at least a portion of the anal sphincter and optionally a cover layer which substantially circumferentially covers an outer surface of the slender member. The slender member optionally includes an active agent for sustained release in the anal canal. The optional cover layer may be a wrapping layer, optionally adhesive, for bandaging and/or wrapping the inner walls of the anal canal to support moist physiological environment. Additionally or alternatively, the cover layer and/or the slender member may include diagnostic and/or active agents for treating and/or diagnosing anorectal disorders. The slender member has a diameter set to push the cover layer toward the inner walls of the anal canal, along the at least a portion of the anal sphincter. The slender member is optionally made from an expandable material, such as a sponge, which is in an expanded state when deployed into the anal canal. Optionally, the medical instrument includes an anchoring portion on its distal end or connected to an anchoring element, referred to herein as anchoring portion. The anchoring portion is wider than the slender member so as to anchor the medical instrument in the anal canal.

According to an aspect of some embodiments of the present invention there is provided an insertion device of inserting a medical instrument of treating or diagnosing anorectal disorders. The insertion device includes a tubular member which is sized for placement into the anal canal, at least along the anal sphincter. The insertion device further includes an applicator that is set to move pivotally within the longitudinal lumen toward the distal end of the tubular member. In such a manner, the applicator may be used for pushing at least a distal portion of a medical instrument located in the tubular member, such as the medical instrument that is outlined above and described below, via the distal end of the tubular member. This allows deploying the medical instrument into the anal canal. Optionally, the tubular member has a rounded distal tip. Optionally, one or more blocking elements are mounted on the tubular member so as to limit the penetration of the insertion device into the anal canal.

According to an aspect of some embodiments of the present invention there is provided a method of inserting a medical instrument of treating or diagnosing an anorectal disorders. The method is based on an insertion device having a tubular member sized for placement into the anal canal, along at least a portion of the anal sphincter, and a medical instrument placed within the tubular member, for example as outlined above and described below. Then, the tubular member of the insertion device is placed in the anal canal so that a distal tip thereof is located along or above the pectinate line, which may be referred to as the dentate line or any line which divides the anal canal. Now, at least a distal end of the medical instrument is pushed, optionally by an applicator, from a longitudinal lumen of the tubular member, into the anal canal. Then, the tubular member is pulled out from the anal canal while the medical instrument remains along at least a portion of the anal canal, in front of its inner walls. During the pulling, the anus applies pressure on the outer surface of the medical instrument, maintaining it in the anal canal.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
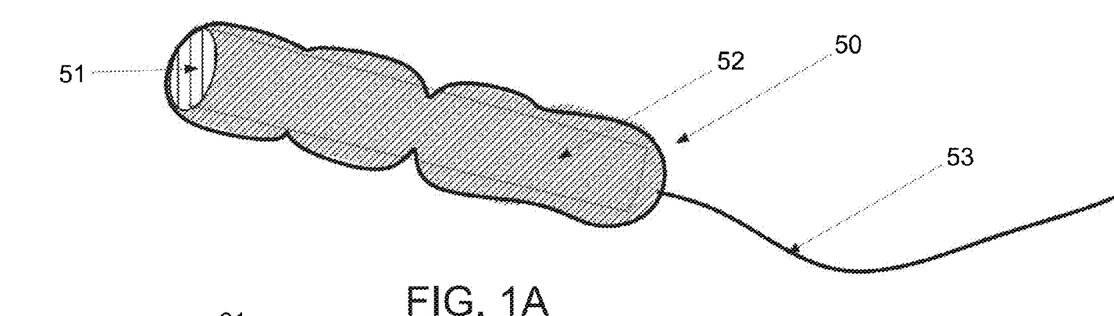
FIG. 1A is a schematic illustration of a medical instrument for treating and/or diagnosing anorectal disorders, according to some embodiments of the present invention.

Reference is now made to FIG. 1A, which is a schematic illustration of a medical instrument 50 for treating and/or diagnosing anorectal disorders, according to some embodiments of the present invention. The medical instrument 50 includes a slender member 51, optionally substantially cylindrical, which is sized and shaped for being placed in a bodily cavity, such as an anal canal, along at least a portion of the anal sphincter. For clarity, anal canal means any portion of the anatomical anal canal. The slender member 51 is optionally expandable and flexible. The slender member 51 is optionally made of a spongy material such as foam, foam rubber, silicon, a biocompatible polymer, such as polyurethane, polypropylene, polyvinyl or polyethylene and/or the like. Optionally, the slender member 51 is biodegradable. In such a manner, the slender member 51 may be compressed to fit into a lumen with a diameter that is thinner than the diameter of an applicator for conducting it to a target location in the anal canal.

The slender member 51 is sized so as to be in contact with and/or to apply pressure on the internal walls of the anal canal, optionally when expanded, along at least a portion of the anal sphincter. Optionally, the cylindrical member 51 is about 3, 4, 5, 6 centimeter or any intermediate or longer length. The slender member 51 optionally comprises a number of sub members. Optionally, the diameter of the slender member 51 in an expanded state is between about 0.4 centimeters and about 0.8 centimeters and between about 0.3 centimeters and about 0.5 centimeters in a compressed state.

Optionally, the medical instrument 50 further comprises a cover layer 52 which substantially circumferentially covers the outer surface of said slender member 51. The cover layer 52 is optionally adhesive, configured to bandage inner walls along at least a portion of the anal sphincter in the anal canal and to optionally to maintain a moist physiological environment therearound.

Optionally, the slender member 51 contains one or more medicaments for treating anorectal disorders by a sustained release of therapeutic agent, for example active agents such as analgesic, anthelmintic, antibacterial, antiviral, antiprotozoal, antidiarrheal, antihemorrhoidal, antimicrobial, hemostatic, anti-inflammatory, a diagnostic aid, a disinfectant, antifungal, an alkylating agent, a muscle relaxant, oxygen enrichment, anti-ischemic agents, chemical debridement, an antacid, a sedative, a mucolytic a contrast media, an antidote, metabolic/endocrinal preparation and/or an anti-cancer agent. Optionally, the slender member 51 contains one or more medicaments, referred to as active agents, using a carrier, for example liposomes, micelles, gelatin, lipids, microcapsules, nanoparticles, nanospheres and microspheres such as poly-lactide-coglycolide (PLGA).

Optionally, the cover layer 52 and/or the slender member 51 are soaked, covered and/or laminated with such medicaments for treating anorectal disorders by a sustained release of therapeutic agent, for example active agents as described above.

In such embodiments, when the medical instrument 50 is placed in the anal canal, it maintains the rectal delivery of the medicament in which the healing process is performed for a period of several hours or even days. The instrument is naturally exit the anal canal with the feces during bowel movement or pulled by the patient as described below.

Optionally, in such embodiments, the cover layer 52 is adapted to facilitate the releasing of therapeutic agent(s) from the slender member 51, optionally, in a sustained manner. For example, the cover layer 52 is perforated with a plurality of apertures, each having a diameter between 0 micron and 50 micron. In such a manner, the medical instrument 50 may be used both for releasing of therapeutic agent(s) and for maintaining a relatively constant humidity level in the proximate portion of the anal sphincter, for example in proximity to the anal sphincter wall around the medical instrument 50.

Optionally, the therapeutic agent is stored in capsules which are placed in the slender member 51. The diameter of the apertures is adapted to prevent the capsules from passing through cover layer 52 while permitting the therapeutic agent to pass therethrough. In such a manner the therapeutic agent is released in a sustained manner while the capsules remain in the slender member 51.

Although most of the description herein is provided in terms of treatment of anal fissure, it is understood that a wide variety of anorectal disorders are treatable with the medical instrument 50. Some of these disorders include hemorrhoids, perianal abscess, perianal fistula, inflammatory bowel disease, gastrointestinal polypoid disease (Peutz-Jaeger Syndrome) and juvenile polypoids, among others. More generally, however, the medical instrument 50 relates to bandaging and/or wrapping lesions of anorectal disorders to support the moist physiological environment and/or the prolonged rectal delivery of any therapeutic active agent, for local and/or systemic delivery.

Optionally, the cover layer 52 and/or the slender member 51 are soaked, covered and/or laminated with one or more therapeutic and/or diagnostic agents such as pharmaceutically active agents, diagnostic reagents, test strips which contain sensitive chromogens or enzyme, and radiopharmaceuticals. In such an embodiment, the medical instrument 50 is used for conducting therapeutic and/or diagnostic agents into the anal canal.

Figure 1B:
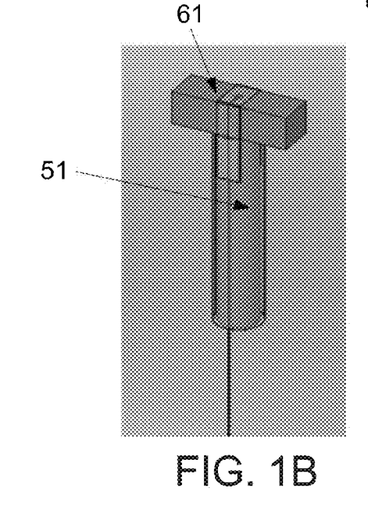
FIG. 1B is a schematic illustration of a medical instrument for treating and/or diagnosing anorectal disorders having an anchoring portion, according to some embodiments of the present invention.
Figure 1C:
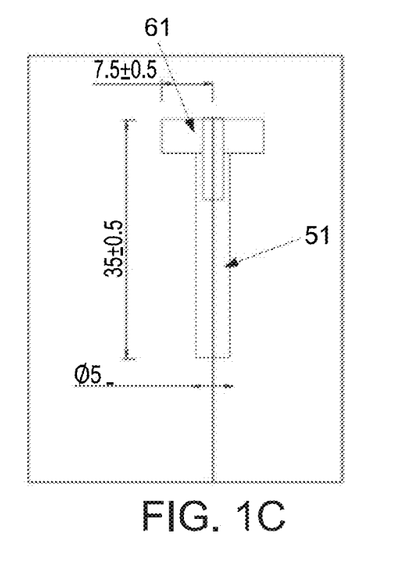
FIG. 1C is a sectional schematic illustration of the sizes of the medical instrument depicted in FIG. 1B, according to some embodiments of the present invention.

Optionally, the medical instrument 50 further comprises an anchoring portion 61 or an anchoring element placed in its distal end, for example as depicted in FIG. 1B. The anchoring portion 61, which may be quadratic, rectangle, tubular, conical, and/or corrugated, is sized so as to anchor the slender member 51 of the medical instrument 50 along the anal sphincter in the anal canal. Optionally, the anchoring portion 61 is set to expend an average width of more than the width the slender member 51. For example, FIG. 1C is sectional illustration of the medical instrument 50 depicted in FIG. 1B which depicts optional sizes of the slender member 51 and the anchoring portion 61. In such a manner, the anchoring portion 61 may expend above the dentate line while the outer surface of the slender member 51 is pressed toward the inner walls of the anal canal. When the medical instrument 50 is disposed in the body of the patient, for example as shown at FIG. 7D, the anchoring portion 61 is above the narrow portion of the anal canal, along the anal sphincter. In such a manner, it can expend to width which is wider than the width of the anal canal along which the slender member 51 is placed. This anchors the medical instrument 50 in place for a period of several hours or even days, until the patient excretes feces.

Optionally, a thread 53 is connected to the slender member 51 of the medical instrument 50, allowing pulling out the instrument manually from the anal canal. Optionally, the thread 53 is biodegradable.

Figure 3A:
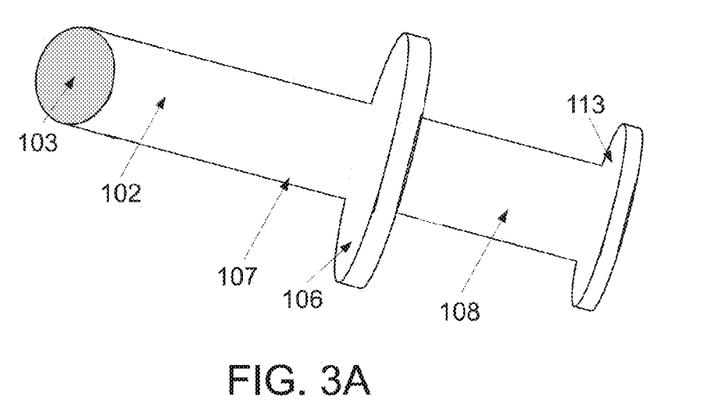
FIGS. 3A-3B are schematic illustrations of a tubular member and an applicator of an insertion device, according to some embodiments of the present invention.
Figure 3B:
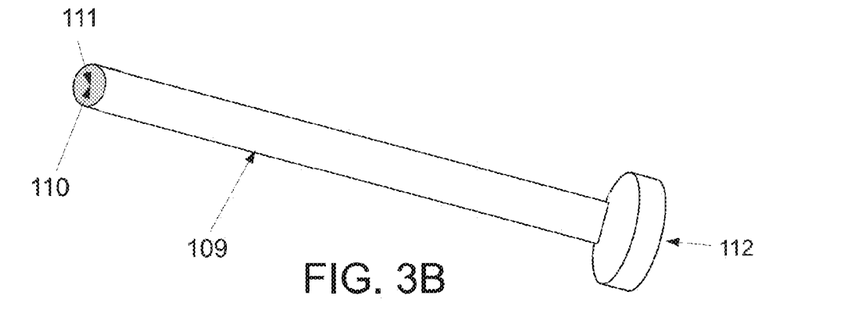
Figures 3C, 3D:
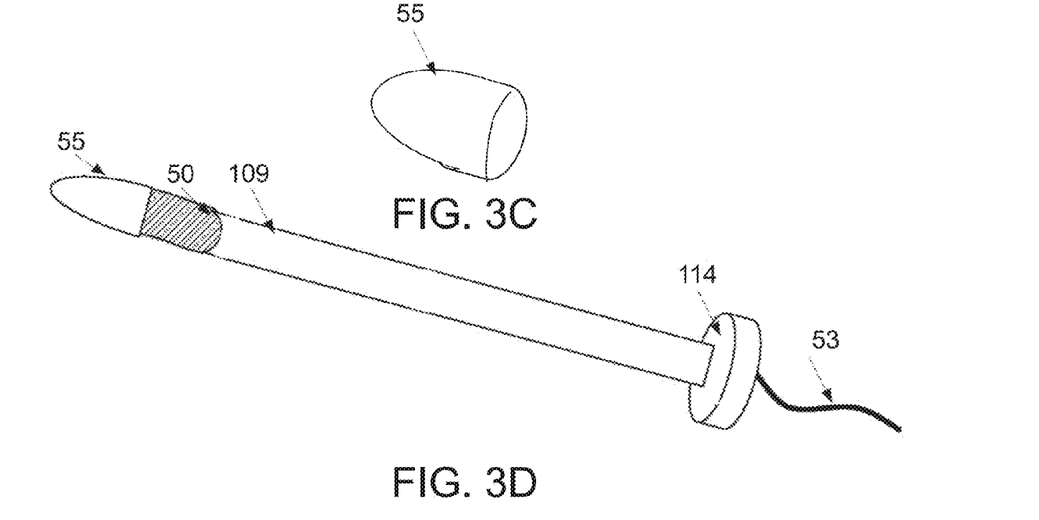
FIG. 3C is a schematic illustration of a dissolvable shell, according to some embodiments of the present invention.
FIG. 3D is the applicator of FIG. 3B with the proximal portion of the medical instrument of FIG. 1A in it lumen and the dissolvable shell of FIG. 3C on its distal portion, according to some embodiments of the present invention.

Optionally, the medical instrument 50 further includes a dissolvable shell 55 for facilitating the insertion thereon into the anal canal. Optionally, the dissolvable shell 55 is shaped as so as to reduce the friction caused during the insertion of the medical instrument 50. For example, FIG. 3C depicts an exemplary dissolvable shell 55 which is shaped as an open cone with a rounded tip. Optionally, the dissolvable shell 55 is made of non-toxic material substantially completely dissolves over a period of several seconds and/or minutes in mammalian body fluids, after the placing thereof in the anal canal. For example, the dissolvable shell 55 may be made of gelatin although one skilled in the art will appreciate that other dissolvable, biocompatible, non-toxic material may be used.

Figure 2:
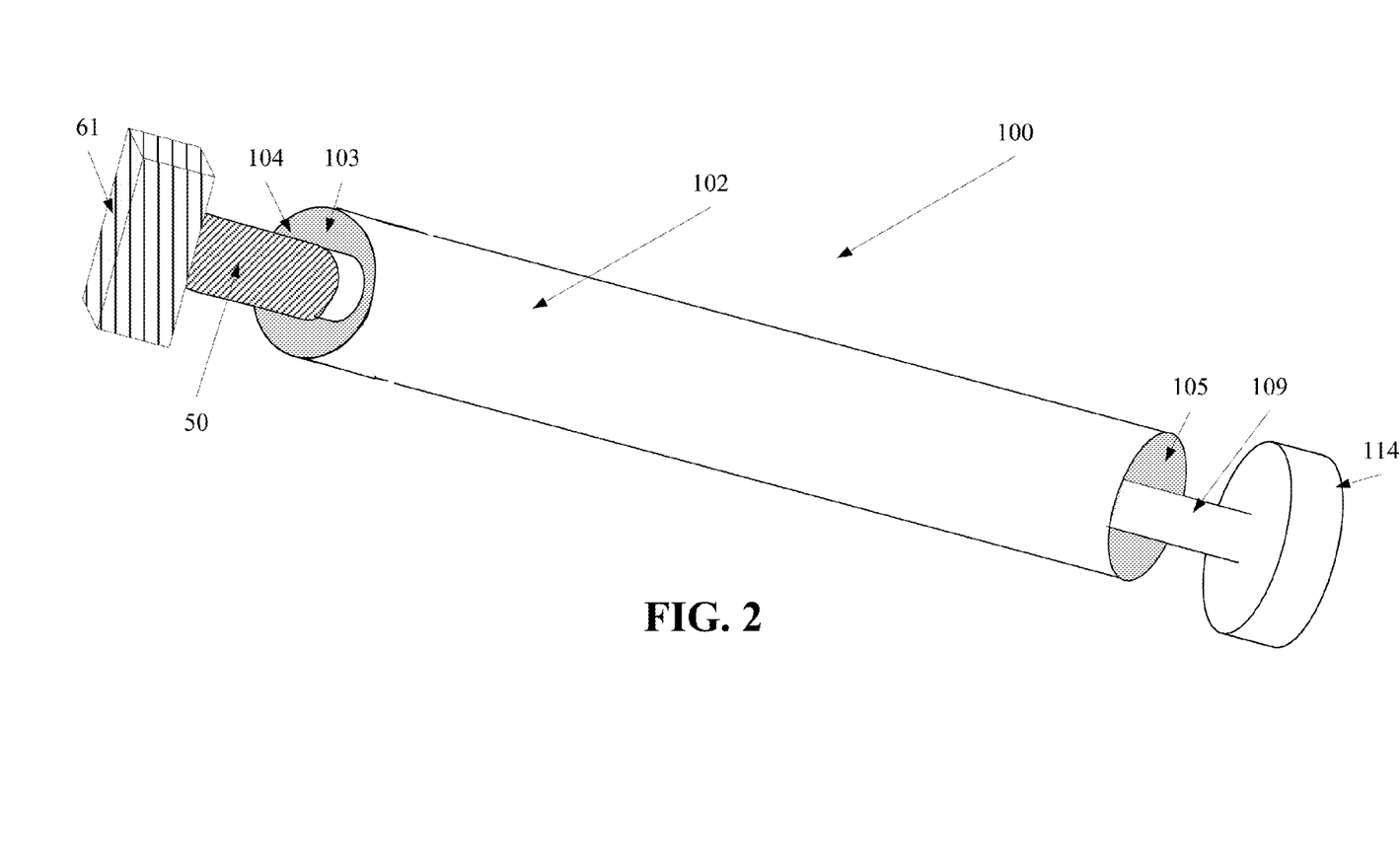
FIG. 2 is a schematic illustration of an insertion device of inserting the medical instrument into a body cavity, such as the anal canal, for example for treating and/or diagnosing anorectal disorders, according to some embodiments of the present invention.

Reference is now also made to FIG. 2, which is a schematic illustration of an insertion device 100 of inserting the medical instrument 50 into a body cavity, such as the anal canal, for example for treating and/or diagnosing anorectal disorders, according to some embodiments of the present invention. The insertion device 100 includes a tubular member 102 which is sized for being placed in a designated body cavity. FIG. 3A depicts such a tubular member. The tubular member 102 has an inner longitudinal lumen 103 and distal and proximal open ends 104, 105. In such a manner, the tubular member 102 can be used for conducting medical instruments for insertion and placement in the designated body cavity. Optionally, the tubular member 102 is made of biocompatible polymers such as polyurethane, silicone elastomer, and/or Polyethene.

Figure 7A:
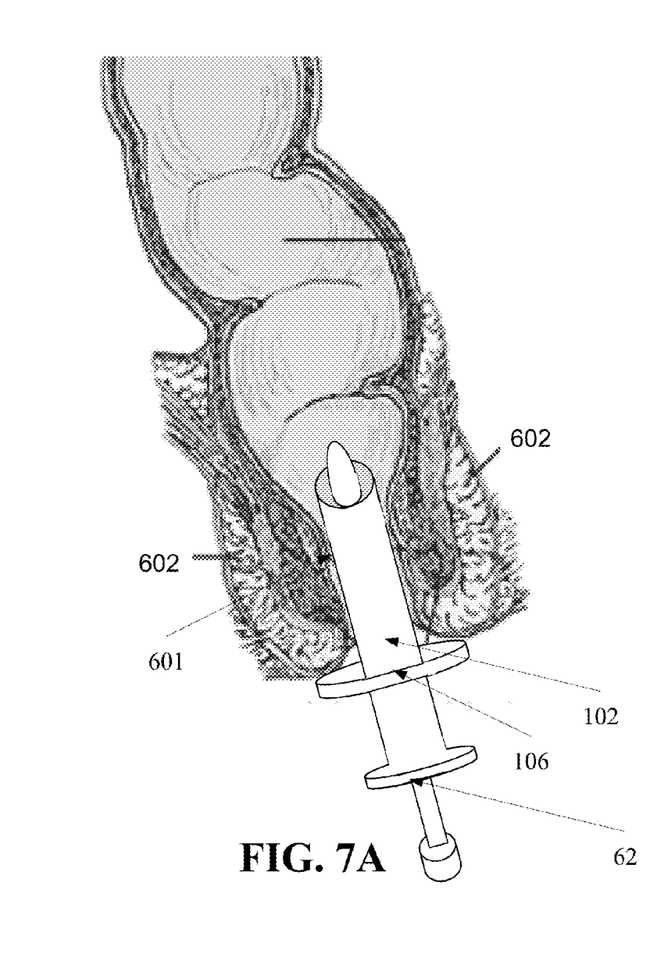
FIGS. 7A-7D, which are schematic cross sectional illustrations of operations made during the implementation of the method depicted in FIG. 6, according to some embodiments of the present invention.

According to some embodiments of the invention, the tubular member 102 is sized for being placed in the anal canal, along the anal sphincter, for example as shown in FIG. 7A. Optionally, the diameter of the inner longitudinal lumen 103 is about 0.5 centimeter, 1 centimeter or any intermediate or wider diameter. Optionally, the length of the inner longitudinal lumen 103 is about 7 centimeter, 8 centimeter, 10 centimeter, 15 centimeter or any intermediate or longer length.

Optionally, one or more blocking elements 106 are mounted on the outer surface of the tubular member 102, optionally circumferentially. Optionally, the one or more blocking elements 106 and the tubular member 102 are molded as a single unit. Optionally, the blocking element 106 is a substantially circular element which circumferentially surrounds a portion of the tubular member 102, as depicted in FIG. 2. The blocking element(s) 106 are located along the tubular member 102 so as to define the depth a caretaker can insert the insertion device 100 in the anal canal. In such a manner, the blocking element(s) 106 divide the tubular member 102 to an insertable potion 107 and an insertion support portion 108 and optionally prevent the inserting of the insertion support portion 108 into the anal canal, for example as shown at FIG. 7A. Optionally, the length of the insertable portion 107 is adapted so that the distal end of the tubular member 102 is placed above the anal canal dentate line, for example as shown at FIG. 7A.

For example, the length of the insertable portion 107 is about 3 centimeter, 4 centimeter, 6 centimeter or any intermediate or longer length. The diameter of the insertion device 100 in the cross section of the blocking elements 106 is wider than the diameter in the cross section of the insertable portion 107.

The insertion device 100 further includes an applicator 109 that is set to move pivotally in the inner longitudinal lumen 103. Reference is also made to FIG. 3B which depicts such an exemplary applicator 109, according to some embodiments of the present invention. Optionally, the applicator 109 is sized to match the diameter of the inner longitudinal lumen 103 in which it is set to move. For example, the external diameter of the applicator 109 is about 0.4 centimeters when the diameter of the inner longitudinal lumen 103 is about 0.5 centimeters. Optionally, the applicator 109 has an inner longitudinal lumen 110 that is sized to receive at least the proximal end of the medical instrument 50, for example as described below and depicted in FIG. 2. Optionally, the applicator 109 has distal and proximal open tips 111, 112 which facilitate placing the medical instrument 50 and optionally its pulling thread 53, for example as shown in FIG. 3D. Optionally, the applicator 109 is made of biocompatible polymers such as polyurethane, silicone elastomer, and/or Polyethene.

Figure 4:
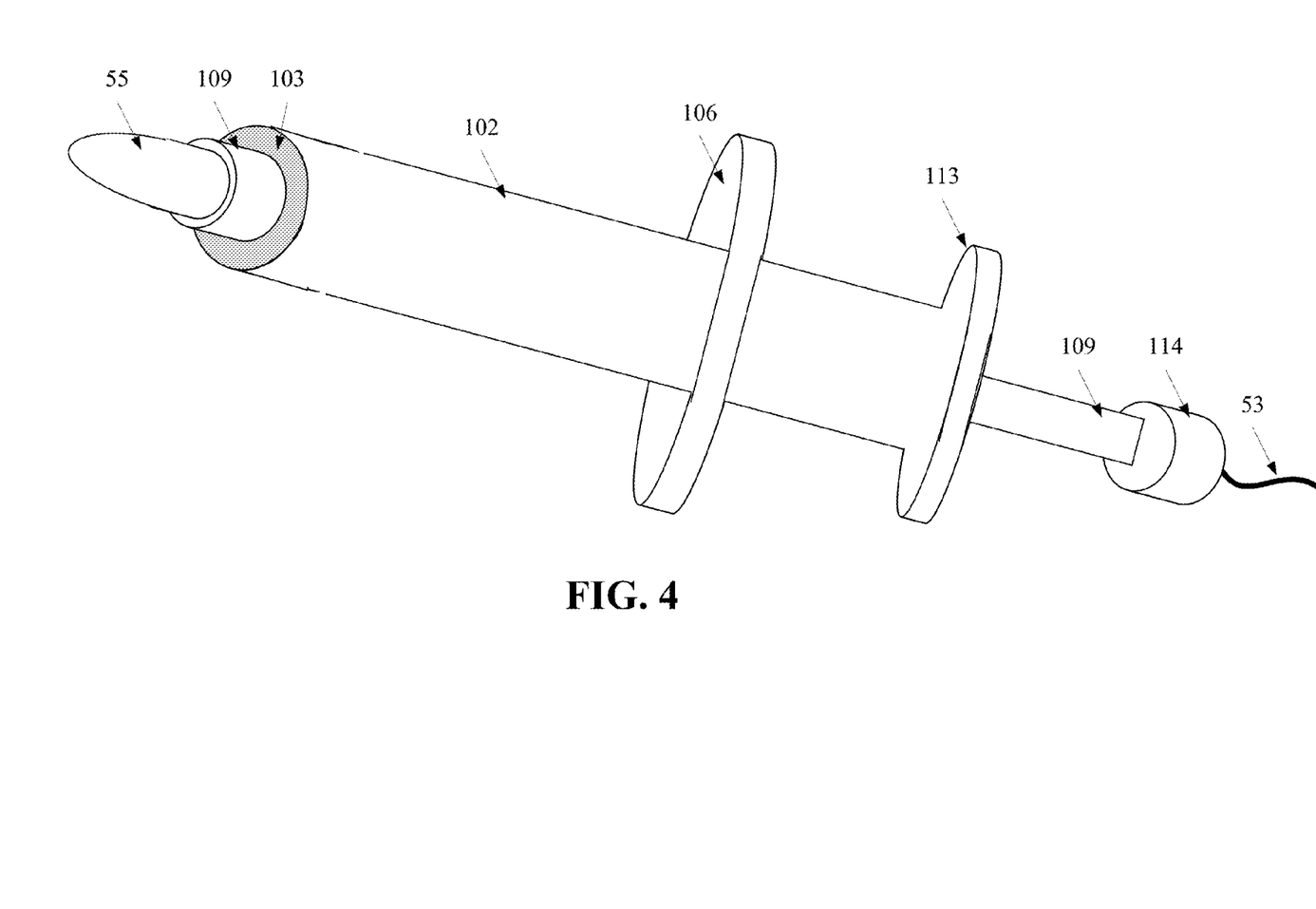
FIG. 4 is a schematic illustration of an insertion device loaded with the medical instrument of FIG. 1A, covered by the dissolvable shell of FIG. 3C, according to some embodiments of the present invention.

Optionally, the applicator 109 surrounds a portion of the slender member 51 as shown in FIG. 3D. In such an embodiment, the insertion device 100 may insert the medical instrument 50 when the dissolvable shell 55 gradually expand the opening diameter of the anus to a diameter which facilitates the insertion of the insertable potion 107 without causing a physical injury to the anus. For example, FIG. 4 depicts the insertion device 100, loaded with the medical instrument 50 which is covered by the dissolvable shell 55, according to some embodiments of the present invention.

The applicator 109 is designed to push the medical instrument 50 outside of the distal end 104. Optionally one or more finger grip(s) 113 are placed on the insertion device 200 for supporting a manual push of the applicator 109 in relation to the tubular member 102. Optionally, the proximal end of the applicator 114 has a wider external diameter than the inner diameter of the inner longitudinal lumen 103 so as to limit the pivotal movement thereof in the inner longitudinal lumen 103.

Reference is now made to FIG. 5, which is a schematic illustration of an insertion device 200 having a tubular member 202 with a semi opened rounded tip 203 for reducing the friction with the anus during an insertion of a medical instrument 50, according to some embodiments of the present invention. The applicator 109, the blocking elements 106, and the finger grip(s) 113 are as described above, however the distal tip 204 of the distal end of the tubular member 202 is shaped to facilitate the extraction of the medical instrument 50 therefrom while supporting a gradual diameter expansion of the anus during the insertion of the insertion device 200 into the anal canal.

Figures 5A, 5B:
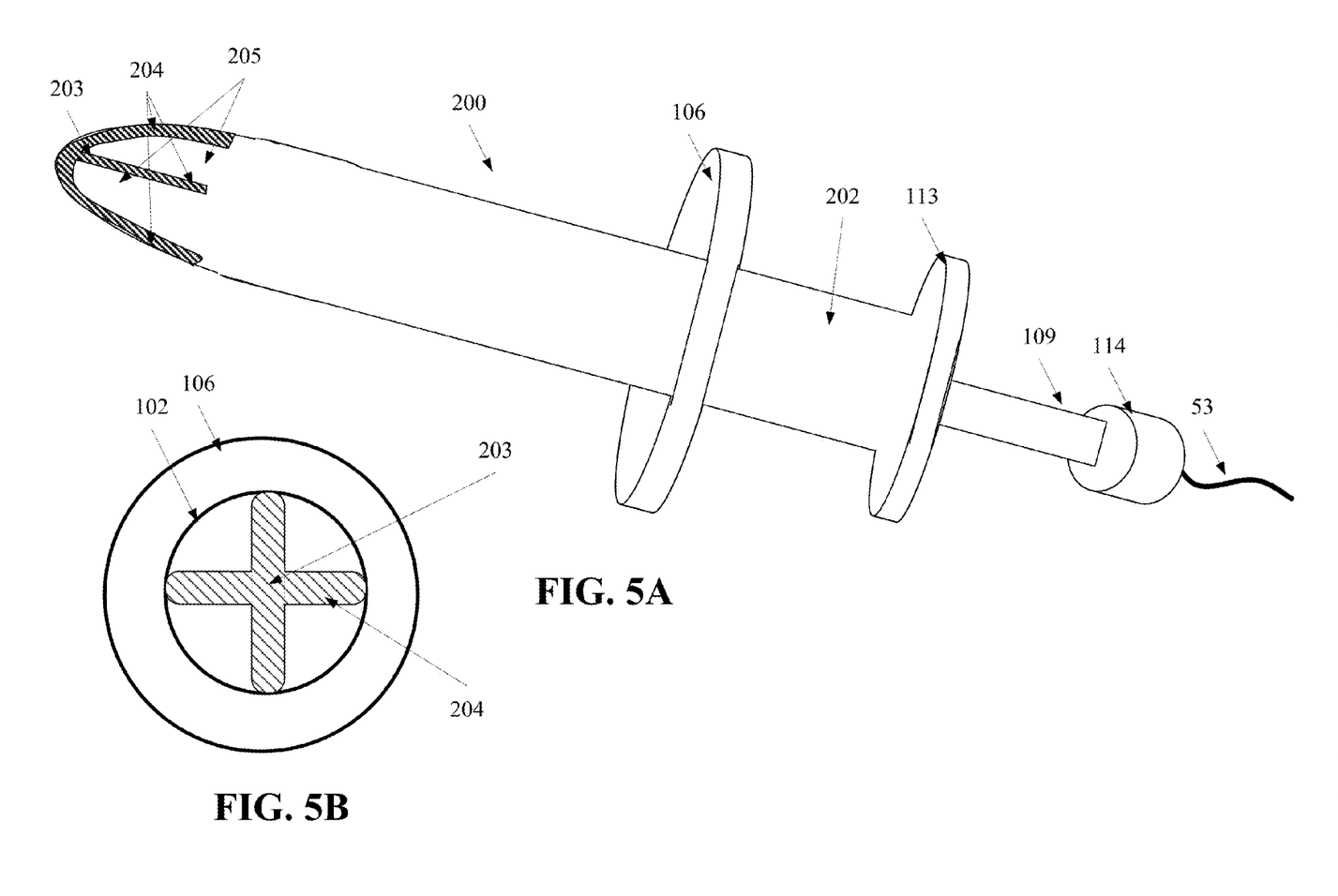
FIGS. 5A and 5B are lateral and top schematic illustrations of an insertion device having a rounded distal end with a plurality of flaps, according to some embodiments of the present invention.
Figure 5C:
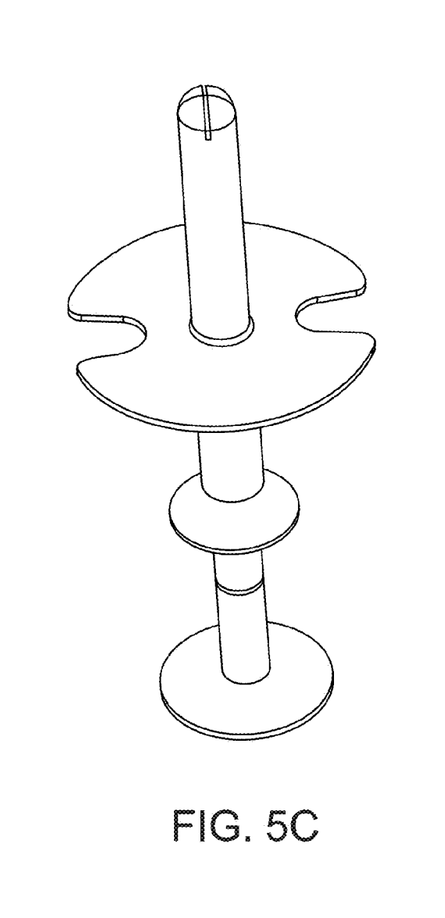
FIG. 5C is a schematic angular illustration of an insertion device having a rounded distal end with a plurality of flaps, according to some embodiments of the present invention.

Optionally, the tip 203 is structured form or includes a plurality of flexible flaps, for example 4. Optionally about 1, 2, 3 millimeters gap 204 is formed between the flaps 205. The rigidity of the flexible flaps 205 allows supporting a conical rounded tip shape during the insertion of the insertion device 200 into the anal canal. When the medical instrument 50, optionally with the dissolvable shell 55, is pushed by the applicator 109 via the tip 203, the flaps are outwardly folded, expanding the gaps 205 and facilitating the passage of the dissolvable shell 55 therethrough. Optionally, the curvature of the tip 203 is shaped with a curvature which matches the curvature of the dissolvable shell 55.

Figure 6:
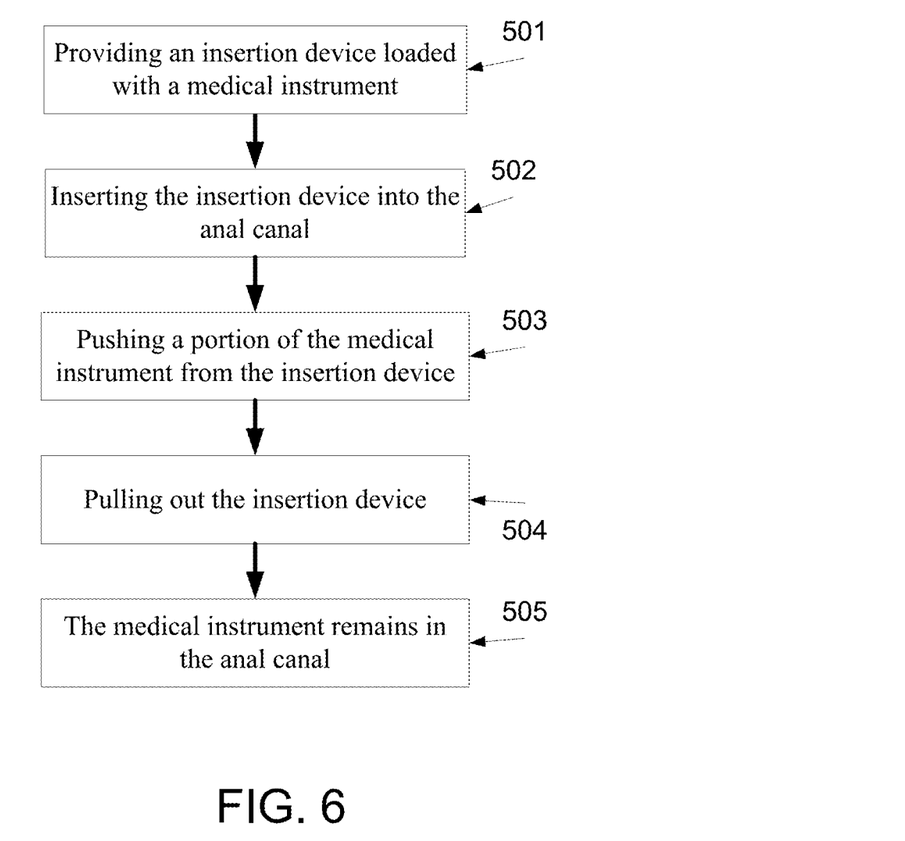
FIG. 6 is a flowchart of a method of inserting a medical instrument for treating one or more anorectal disorders to the anal canal, according to some embodiments of the present invention.

Reference is now also made to FIG. 6, which is a flowchart of a method 500 of inserting a medical instrument for treating one or more anorectal disorders to the anal canal, according to some embodiments of the present invention. Reference is also made to FIG. 2 and to FIGS. 7A-7D, which are schematic cross sectional illustrations of operations made during the implementation of the method 500 depicted in FIG. 6, according to some embodiments of the present invention, using the exemplary insertion device 100 depicted in FIG. 2 and the exemplary medical instrument 50 depicted in FIG. 1A.

First, as shown at 501, an insertion device, such as the insertion device 100, loaded with the medical instrument 50. The medical instrument 50 is placed so that its distal end is in the inner longitudinal lumen 103 and its proximal end is optionally in the inner lumen of the applicator 109.

Now, as shown at 502, the insertion device 100 is inserted into the anal canal 601 to the anal canal so that the insertable portion 107 thereof is placed along at least a portion of the anal sphincter 602 and the tip of the tubular member 102 is located along at least a portion of the anal sphincter 602 and/or above the anal dentate line, for example as shown at FIG. 7A.

Figure 5D:
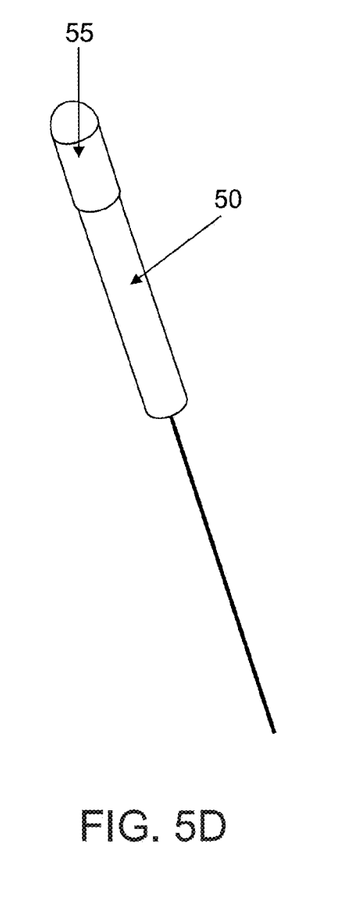
FIG. 5D is a schematic illustration of a slender member, having a dissolvable shell on its tip and a thread, adapted for being placed in the anal canal by the insertion device depicted in FIG. 5C, according to some embodiments of the present invention.
Figure 5E:
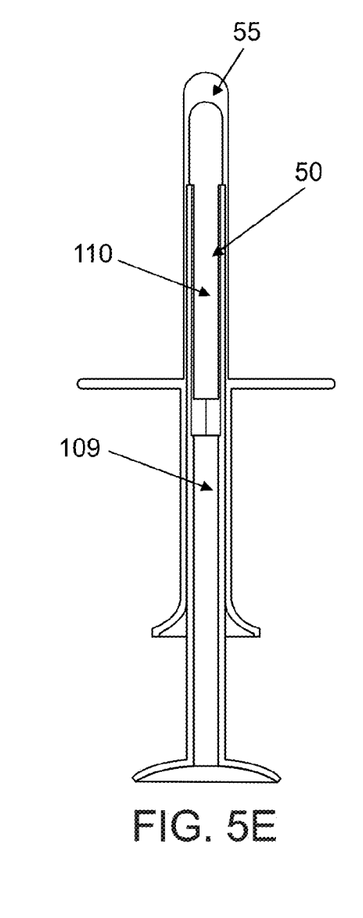
FIG. 5E is a sectional view of the insertion device depicted in FIG. 5C, according to some embodiments of the present invention.
Figure 7B:
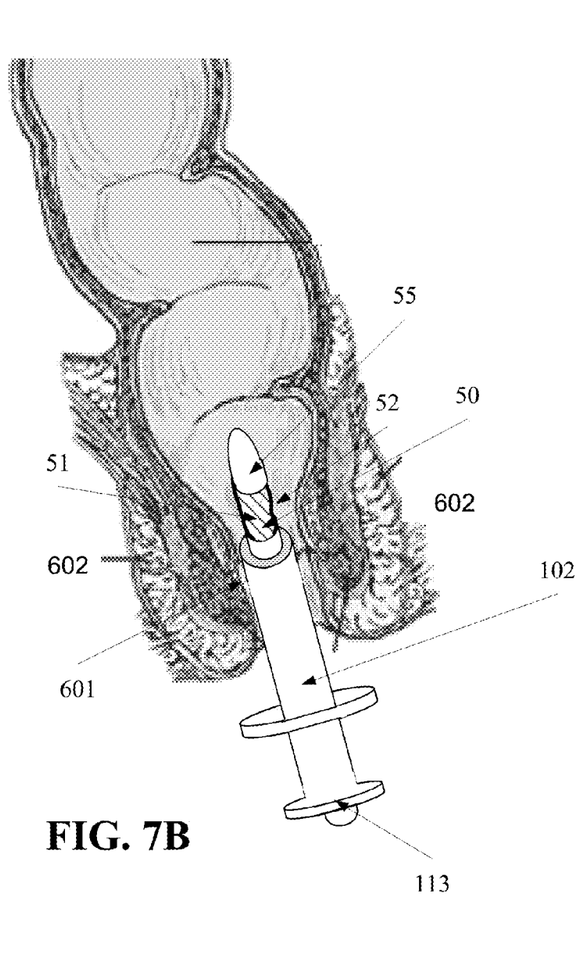

As shown at 503, the applicator 109 is pivotally moved in the longitudinal lumen 103 so as to push and extract at least a distal portion of the medical instrument 50 from the distal end 104 of the tubular member 102, in the anal canal, for example as shown at FIG. 7B. The moving of the applicator 109 is optionally manually performed by pushing the applicator toward the tubular member 102, like moving a piston toward the barrel of a syringe. Optionally, the extracted portion of the medical instrument 50 is covered by a dissolvable shell 55. Optionally, the distal end 104 is rounded and comprises a plurality of flaps 205, as shown at FIGS. 5A, 5B, and 5C. In such an embodiment, the pushing of the medical instrument 50 folds the flaps 205 outwardly. Optionally, as shown at FIG. 5D, the medical instrument 50, which is covered by the dissolvable shell 55, is sized and shaped to fit in the tubular member 102. Optionally, as shown at FIG. 5E, which is a sectional view of the insertion device depicted in FIG. 5C, the proximal end 62 of the medical instrument 50 is sized and shaped to be placed in the inner longitudinal lumen 110 of the applicator 109.

Figure 7C:
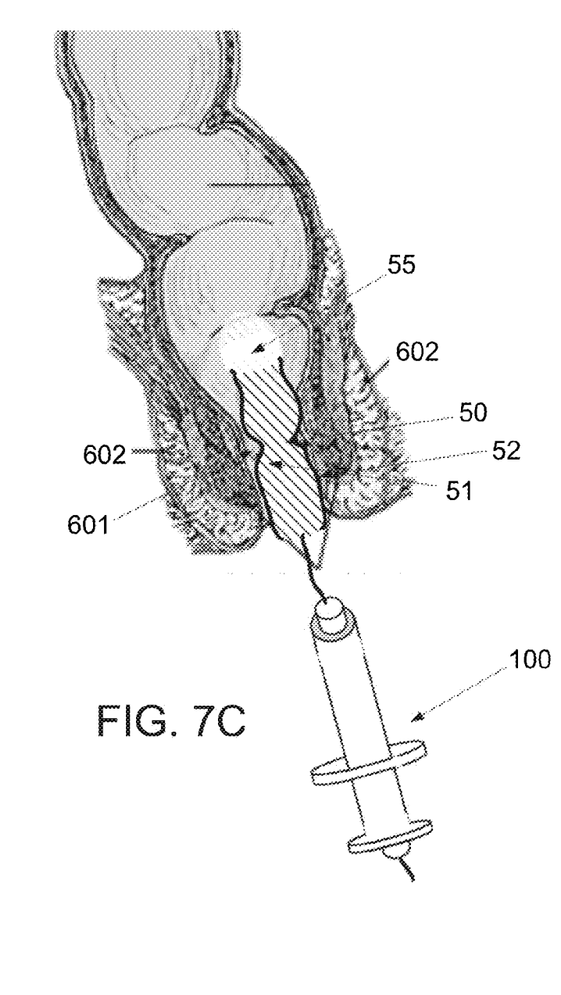
Figure 7D:
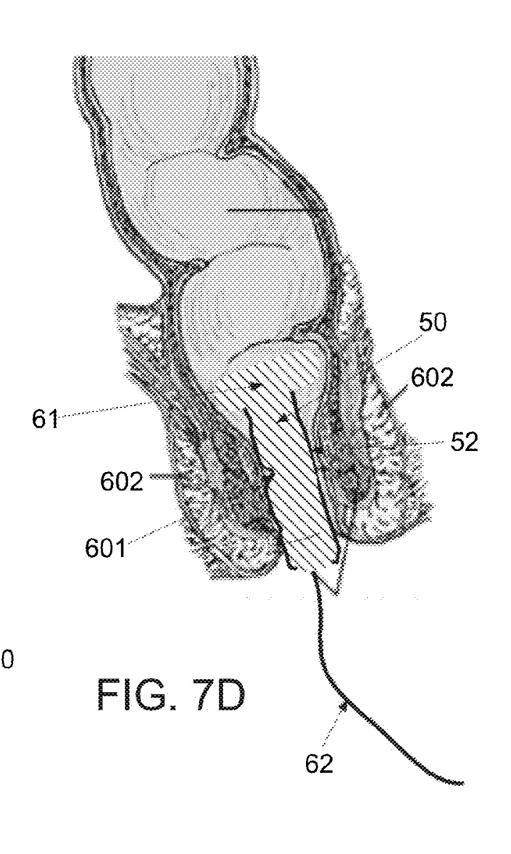

Now, as shown at 504 and in FIG. 7C, the insertion device 100 is pulled from the anal canal 601 while the medical instrument 50 remains along at least a portion of the anal sphincter. As shown in FIG. 7C the medical instrument 50 and the dissolvable shell (shown in a slightly dissolved state) remain into the anal canal 601. The shell dissolves with time and the medical instrument 50 may be placed to bandage or wrap the inner walls of at least a portion of the anal canal and/or release therapeutic and/or diagnostic active agents, for example as described above. As described above and depicted in FIGS. 7A and 7B, the insertion device is optionally placed so that the distal end 104 is above the anal dentate line. The anal pressure ensures that the medical instrument 50 remains into the anal canal after the insertion device 100 is pulled away from the anus. FIG. 7D depicts the medical instrument 50 deployed in the anal canal 601, along the anal sphincter 602. Optionally, as shown at 505, the medical instrument 50 remains in the anal canal of the patient for a period of several hours or even days, until the patient excretes feces. As shown at FIG. 7D, the dissolvable shell 55 dissolves while the medical instrument 50 is in the anal canal, along the anal sphincter.

It is expected that during the life of a patent maturing from this application many relevant devices, components, and methods will be developed and the scope of the term medicament, agent, dissolvable material, and a spongy material is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A medical instrument for treating and/or diagnosing anorectal disorders, comprising:
   a slender member sized and shaped for being placed in the anal canal of a patient, along at least a portion of the anal sphincter; and
   a cover layer having a plurality of apertures, said cover layer substantially circumferentially covers an outer surface of a proximal end of said slender member, said slender member having a diameter set to push said cover layer so that when said medical instrument is located in said anal canal and a distal end of said slender member is above the anal dentate line, said cover layer is in contact with inner walls of said anal canal therearound;
   a dissolvable shell sized to cover at least said distal end of said slender member;
   wherein after said shell dissolves in the anal canal of said patient, an anchoring portion of said distal end expands to width which is wider than the width of the rest of the slender member in the anal sphincter;
   wherein when said medical instrument is located in said anal canal and said distal end is above the anal dentate line, said cover layer bandaging said inner walls to maintain a relatively constant humidity level in a proximate portion of the anal sphincter.

2. The medical instrument of claim 1, wherein said slender member contains an active agent for a sustained release along said portion.

3. The medical instrument of claim 2, wherein said active agent is selected from a group consisting of analgesic, anthelmintic, antibacterial, antiviral, antimicrobial, antiprotozoal, antidiarrheal, antihemorrhoidal, antihemorrhoidal, hemostatic, anti-inflammatory, a diagnostic aid, a disinfectant, antifungal, an alkylating agent, muscle relaxants, oxygen enrichment, vasodilators, anti-ischemic agents, chemical debridement, hormones, growth factors, cytokines and other bioactive peptidic compounds, an antacid, a sedative, a mucolytic a contrast media, an antidote, metabolic/endocrinal preparation and an anti-cancer agent.

4. The medical instrument of claim 1, wherein said plurality of apertures are sized so as to allow a sustained release of said active agent therethrough.

5. The medical instrument of claim 1, wherein each said plurality of apertures has a diameter of between 0 micron and 50 micron.

6. The medical instrument of claim 1, wherein said active agent is encapsulated in a plurality of capsules placed in said slender member and each said plurality of apertures is sized so as to allow a sustained release of said active agent therethrough while said plurality capsules remains in said slender member.

7. The medical instrument of claim 3, further comprising an anchoring element, placed above the distal end of said slender member, said anchoring element is wider than said slender member when disposed in said anal canal.

8. The medical instrument of claim 1, further comprising a thread connected to said slender member so as to allow pulling out said slender member by the patient.

9. The medical instrument of claim 1, wherein said slender member comprising a plurality of sub elements threaded on a common thread.

10. The medical instrument of claim 1, wherein at least one of said cover layer and said slender member is at least one of soaked, covered and laminated with an active agent.

11. The medical instrument of claim 1, wherein at least one of said cover layer and said slender member is at least one of soaked, covered and laminated with at least one diagnostic agents.

12. The medical instrument of claim 1, wherein said slender member is expandable and said diameter is achieved when said slender member is in an expanded state.

13. The medical instrument of claim 1, wherein said medical instrument is part of a kit that comprises an insertion device for inserting said medical instrument, said insertion device comprising:
 a tubular member sized for placement in the anal canal, at least along the anal sphincter and having a longitudinal lumen and a distal end; and
 an applicator pivotally movable within said longitudinal lumen toward said distal end so as to push at least a distal portion of a medical instrument via said distal end, said medical instrument being insertable within said longitudinal lumen and sized for being substantially placed in the anal canal along the anal sphincter.

14. The insertion device of claim 13, wherein said applicator has an inner lumen which is sized for surrounding at least a proximal portion of said medical instrument.

15. The insertion device of claim 13, wherein said distal end having a rounded tip.

16. The insertion device of claim 13, further comprising at least one blocking element mounted on the circumferential outer surface of said tubular member so as to locate said distal end above the anal dentate line when said tubular member is placed in the anal canal.

17. The insertion device of claim 13, wherein said distal end has a first average diameter and the rest of said tubular member having a second average diameter, said first average diameter being smaller than said second average diameter.

18. The insertion device of claim 13, wherein said distal end having a tip with at least one flexible flap configured for being pushed by said medical instrument when said medical instrument being extracted from said tip.

19. The insertion device of claim 18, wherein said at least one flexible flap form a semi rigid structure which does not substantially collapse when said tubular member is placed in the anal canal.

20. The insertion device of claim 18, wherein said at least one flexible flap is rounded.

21. A medical instrument for treating and/or diagnosing anorectal disorders, comprising:
 a slender member sized and shaped for being placed in the anal canal of a patient, along at least a portion of the anal sphincter;
 a dissolvable shell sized to cover at least a distal end of said slender member;
 an active agent disposed in said slender member; and
 a cover layer substantially circumferentially covering an outer surface of a proximal end of said slender member and perforated with a plurality of apertures;
 wherein said slender member having a diameter set to push said cover layer so that when said medical instrument is located in said anal canal and said distal end of said slender member is above the anal dentate line, said cover layer is in contact with inner walls of said anal canal therearound;
 wherein when said medical instrument is located in said anal canal and said distal end of said slender member is above the anal dentate line, said cover layer bandaging said inner walls of said anal canal to maintain a relatively constant humidity level in a proximate portion of the anal
 wherein said plurality of apertures are set so as to allow a release of said active agent therethrough;
 wherein after said shell dissolves in the anal canal of said patient, an anchoring portion of said distal end expands to width which is wider than the width of the rest of the slender member in the anal sphincter.

22. The medical instrument of claim 21, wherein each said plurality of apertures has a diameter of between 0 micron and 50 micron.

23. The medical instrument of claim 21, wherein said slender member is sized and shaped so that an outer surface of said cover layer is in contact with inner walls of said anal canal.

* * * * *